US009123515B2

(12) United States Patent
Fujita (10) Patent No.: US 9,123,515 B2
(45) Date of Patent: Sep. 1, 2015

(54) ION MOBILITY SPECTROMETER (71) Applicant: SHIMADZU CORPORATION, Kyoto-shi, Kyoto (JP)

(72) Inventor: Ryo Fujita, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 0 days.

(21) Appl. No.: 14/506,967

(22) Filed: Oct. 6, 2014

(65) Prior Publication Data

US 2015/0108345 A1 Apr. 23, 2015

(30) Foreign Application Priority Data

Oct. 21, 2013 (JP) ................. 2013-218547

(51) Int. Cl.
H01J 49/06 (2006.01)
G01N 27/62 (2006.01)
H01J 49/04 (2006.01)

(52) U.S. Cl.
CPC ............ *H01J 49/062* (2013.01); *G01N 27/622* (2013.01); *H01J 49/04* (2013.01)

(58) Field of Classification Search
USPC ................................. 250/286, 287
See application file for complete search history.

(56) References Cited

U.S. PATENT DOCUMENTS

| 4,150,319 A | 4/1979 | Nowak et al. | |
|---|---|---|---|
| 2010/0200745 A1* | 8/2010 | Osgood et al. | 250/282 |
| 2014/0346346 A1* | 11/2014 | Wu et al. | 250/287 |

FOREIGN PATENT DOCUMENTS

| JP | 2733750 B | 3/1998 |
|---|---|---|
| JP | 2005-174619 A | 6/2005 |

* cited by examiner

Primary Examiner — Kiet T Nguyen
(74) Attorney, Agent, or Firm — Sughrue Mion, PLLC (57) ABSTRACT Shutter gate grid is a structure wherein first and second disc-shaped members made of metal with an insulation sheet member sandwiched therebetween are integrally joined by means of insulative screws. Gate grids with conductive wires secured to the central openings thereof are fused onto the disc-shaped members; screw insertion holes formed in the second disc-shaped member are fan-shaped and have play in the direction of rotation, making it possible to adjust the parallelism of the conductive wires of the two members by finely adjusting the rotational position when tightening the screws. Moreover, diffusion gas can be made to flow through ventilation holes provided at common locations on each member, thus making it possible to provide uniformity of diffusion gas flow in the drift region.

7 Claims, 4 Drawing Sheets

ION MOBILITY SPECTROMETER

TECHNICAL FIELD

The present invention relates to an ion mobility spectrometer.

BACKGROUND ART

Figure 5:
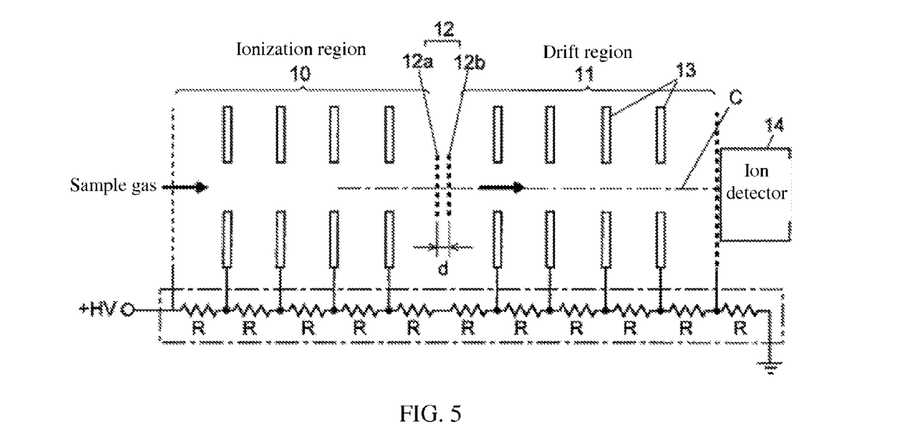
FIG. 5 A schematic diagram of a common ion mobility spectrometer.

When molecular ions generated from sample molecules are moved through a gas (or liquid) medium due to the action of an electric field, those ions move at a velocity proportional to their mobility, which is determined by the strength of the electric field, the size of the molecules, etc. Ion mobility spectrometry (IMS) is a measurement method which employs this mobility for analysis of sample molecules. FIG. 5 is a schematic of a common ion mobility spectrometer disclosed in Patent Literatures 1 and 2 and the like.

An ion mobility spectrometer comprises, inside, for example, an unillustrated round tubular housing, an ionization region 10 for ionizing component molecules in a sample, a drift region 11 for measuring the movement velocity of the ions, and a detector 14 which detects ions flying through the drift region 11. Furthermore, a shutter gate grid 12 is provided at the boundary between the ionization region 10 and the drift region 11 for feeding the ions generated in the ionization region 10 into the drift region 11 in the form of pulses limited to a very short time width.

Figure 6:
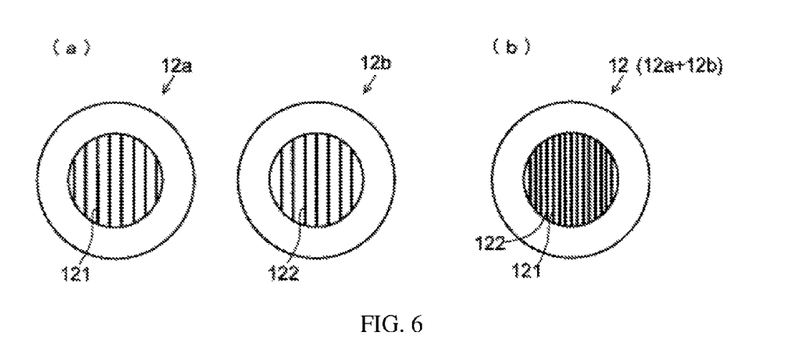
FIG. 6 A schematic of the grid electrodes of FIG. 5 viewed from the ion introduction direction.

The shutter gate grid 12 comprises a pair of grid electrodes 12a, 12b provided spaced apart at a predetermined interval d in the ion passage direction. FIG. 6 (a) is a schematic of the grid electrodes 12a, 12b viewed from the ion introduction direction. In this example, the grid electrodes 12a, 12b consist of multiple conductive wires 121, 122 which are stretched in parallel in the same plane. Conductive wires 122 in the rear grid electrode 12b are provided right in middle of two adjacent conductive wires 121 of the front grid electrode 12a, so when a pair of grid electrodes 12a, 12b is viewed from the ion introduction direction, as shown in FIG. 6 (b), the conductive wires 122 are lined up substantially at equal intervals, and the space between adjacent conductive wires 122 constitutes a slot-shaped opening through which ions can pass (for example, see FIG. 7 of Patent Literature 2).

In the above ion mobility spectrometer, an electric field (an electric field which accelerates ions) which exhibits a downward potential gradient in the ion travel direction is formed in the drift region 11 due to the direct current voltage applied to the annular electrodes 13 arranged in the ionization region 10 and drift region 11. When sample components in the sample gas are introduced into the ionization region 10, they are ionized in the ionization region 10 by the action of β rays emitted from a β ray source ($^{63}$Ni, etc.) or the like. When ions generated in this manner pass through the shutter gate grid 12 and are introduced into the drift region 11 only in periods of very short time width, the ions proceed along a downward potential gradient. Furthermore, while not illustrated, diffusion gas flow in a direction opposite to the ion travel direction is formed in the drift region 11, and the ions move while colliding with this diffusion gas. In the process of this movement, the ions are separated according to their size, etc., and ions of different size arrive at the detector 14 with a time difference. The resolution of ion mobility spectrometry depends to a great extent on the time width (pulse width) of ions passing through the shutter gate grid 12, so in order to increase the resolution, it is necessary to make the pulse width of ions at the shutter gate grid 12 as short as possible.

Figure 7:
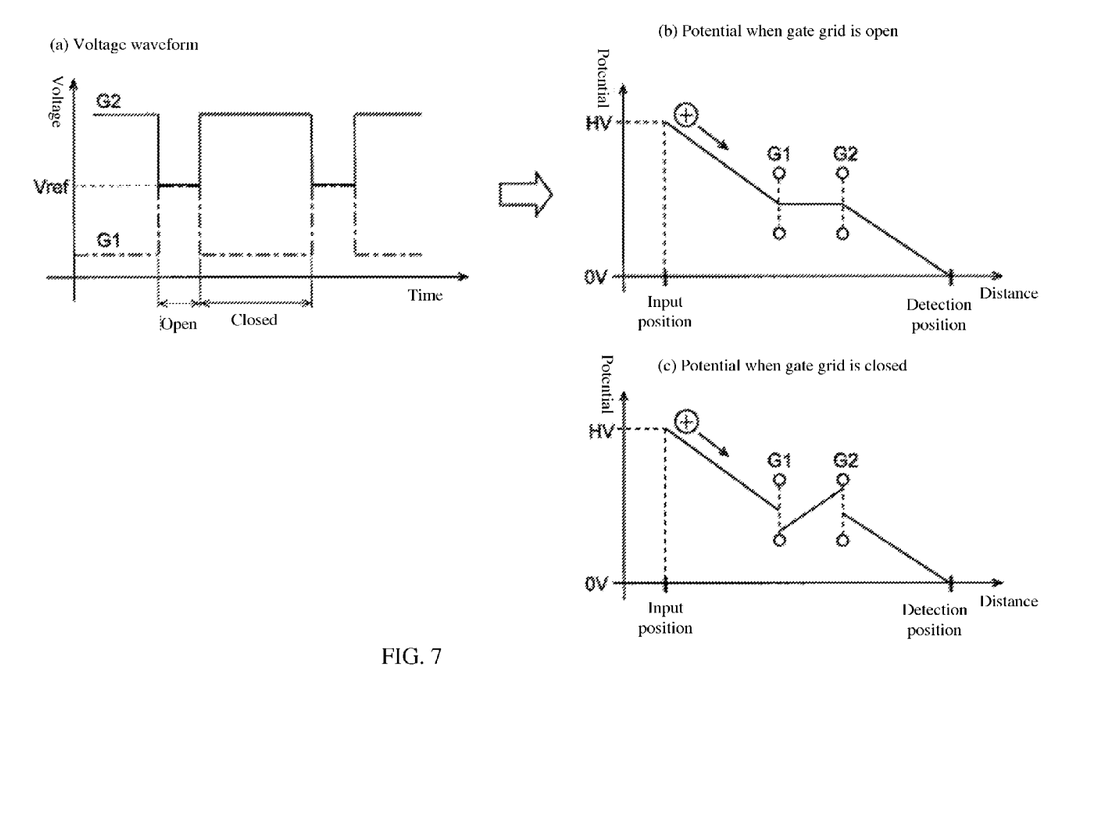
FIG. 7 A schematic of the waveform of voltage applied to the grid electrodes and the potential gradient on the ion optical axis in a conventional ion mobility spectrometer.

FIG. 7 is a schematic of the potential gradient in the ion optical axis direction and the voltage applied to the pair of grid electrodes 12a, 12b. In this example, ions of positive polarity are assumed. When an identical voltage (Vref) is applied to the front grid electrode 12a and the rear grid electrode 12b, the shutter gate grid 12 assumes a substantially open state (see FIG. 7 (b)), and the ions pass through the shutter gate grid 12 and flow into the drift region 11. On the other hand, when voltage is applied to the grid electrodes 12a, 12b so as to make the potential of the rear grid electrode 12b several hundred V higher than the potential of the front grid electrode 12a, the shutter gate grid 12 assumes a substantially closed state (see FIG. 7 (c)) as a result of this potential barrier, and the ions are blocked by the shutter gate grid 12. Generally, the open time of the shutter gate grid 12 is several hundred μsec to several msec, and the opening frequency is about several tens of msec.

In order to narrow the pulse width of ions in a shutter gate grid 12 consisting of a pair of grid electrodes 12a, 12b as described above, it is necessary to make the separation distance d between the grid electrodes 12a, 12b as small as possible while avoiding contact between the conductive wires of the different grid electrodes. Furthermore, in order to obtain a high ion throughput efficiency, it is necessary to use conductive wires 121, 122 which are as thin as possible and to arrange multiple such wires in parallel at a narrow gap. To do this, high mechanical precision is required for the arrangement of the grid electrodes 12a, 12b and the conductive wires 121, 122 in each grid electrode. However, when the shutter gate grid is in a closed state, as described above, quite a large voltage difference is applied to the pair of grid electrodes 12a, 12b, so the force produced by the electric field acts upon the conductive wires, and the conductive wires of the front grid electrode 12a and the conductive wires of the rear grid electrode 12b are attracted toward each other. For this reason, it is difficult to precisely maintain the separation distance d of the grid electrodes 12a, 12b.

A technique for arranging multiple conductive wires in rows in a plane with high precision while avoiding contact between conductive wires of different grid electrodes and making the separation distance d as small as possible is disclosed in Patent Literature 3. Here, holes are formed at suitable locations in a flange extending from the inner circumferential side of an annular member composed of an insulator, and two long conductive wires are passed through different holes, thereby forming rows of parallel conductive wires in one plane, corresponding to one grid electrode, and forming rows of parallel conductive wires on another plane, corresponding to the other grid electrode.

However, a shutter gate grid of this sort has a complex structure, and the assembly operation is time-consuming. Thus, it has the problem of increased cost.

Furthermore, since an insulative material is located very close to the ion flow passing through the shutter gate grid, there is the problem that charge-up occurs readily due to the ions contacting the insulative material.

Moreover, since the flange extending from the inner circumferential side of the annular member narrows the channel for the diffusion gas which flows opposite to the ion flow, there is the problem that the flow velocity of the diffusion gas becomes too great and resolution is reduced.

In addition, since the diffusion gas flows only in the central portion of the housing inside which the drift region is formed, charge-up and contamination tend to remain near the walls of the housing, so much time is expended on the initial conditioning, and there is the concern that such contamination may affect analytical sensitivity and resolution.

PRIOR ART LITERATURES

Patent Literatures (Patent Literature 1) Japanese Patent No. 2733750
(Patent Literature 2) Japanese Unexamined Patent Application Publication 2005-174619
(Patent Literature 3) U.S. Pat. No. 4,150,319

SUMMARY OF THE INVENTION

Problem to be Solved by the Invention

The present invention was made to resolve the above problems, its main purpose being to provide an ion mobility spectrometer comprising a shutter gate grid having a simple structure that is easy to fabricate, wherein a pair of grid electrodes are arranged with high mechanical precision and the separation distance between them is made small while avoiding contact.

Means for Solving the Problem

The present invention, which was made to resolve the above problems, is an ion mobility spectrometer comprising an ionization section which generates ions derived from sample components, a drift region which causes the ions generated in the ionization section to move such that they separate according to mobility, and a shutter gate grid for extracting the ions in short pulses and feeding them to said drift region, characterized in that said shutter gate grid comprises:

a first conductive disc-shaped member wherein multiple conductive wires are secured in parallel in a central opening and multiple threaded holes are formed in the periphery; a second conductive disc-shaped member wherein multiple conductive wires are secured in parallel in a central opening and multiple fan-shaped screw insertion holes are formed in the periphery; and an insulation sheet member which has a central opening and multiple screw insertion holes formed in the periphery, wherein, in a state where said insulation sheet has been sandwiched between said first conductive disc-shaped member and said second conductive disc-shaped member, these members are integrally joined by means of a plurality of screws having electrical insulative characteristics, which are inserted in sequence through the fan-shaped screw insertion holes of said second conductive disc-shaped member, the screw insertion holes of said insulation sheet member, and into the threaded holes of said first conductive disc-shaped member.

Any method can be used for securing the conductive wires in the first and second conductive disc-shaped members so long as conductivity can be ensured, but typically, the conductive wires can be suitably secured to the disc-shaped members by being fused on through welding or the like. The parallelism of the conductive wires corresponding to one grid electrode is determined by the precision of securement of the conductive wires to the disc-shaped member, so it is desirable to secure the conductive wires with a high positional precision.

In the ion mobility spectrometer of the present invention, the first conductive disc-shaped member and the second conductive disc-shaped member are integrally joined by means of screws in a state where an insulation sheet has been sandwiched between said two members, so the distance between the conductive wires secured to the first conductive disc-shaped member and the conductive wires secured to the second conductive disc-shaped member is determined by the thickness of the insulation sheet. Namely, the separation distance between a pair of grid electrodes to which different voltages can be applied is determined with a high precision by the thickness of the insulation sheet.

Furthermore, the positional relationship between the first conductive disc-shaped member and the second conductive disc-shaped member in the direction of rotation (the direction of rotation centered about an axis orthogonal to the two members) can be adjusted on account of the play in the direction of rotation of the fan-shaped screw insertion holes formed in the second conductive disc-shaped member. Therefore, when integrally joining these disc-shaped members by means of screws, the parallelism of conductive wires in the different planes can be ensured with high precision by adjusting the position in the direction of rotation such that the conductive wires secured to the respective members become parallel to each other.

In this way, with the ion mobility spectrometer of the present invention, it is possible to determine separation distance between the pair of grid electrodes, the gap between adjacent conductive wires and the like with high precision using a simple structure having high ease of assembly. Furthermore, with the shutter gate grid in the ion mobility spectrometer according to the present invention, the portions exposed to ions are mainly conductors, so the likelihood of charge-up occurring is low.

Furthermore, in the ion mobility spectrometer according to the present invention, preferably, the first and second conductive disc-shaped members are made in a configuration having threaded holes for securing electric wires.

This makes it possible to easily perform electric wiring of the conductive disc-shaped members and improves the ease of assembly.

Furthermore, the ion mobility spectrometer according to the present invention may be configured such that multiple electrodes for forming an electric field, which are conductive disc-shaped members having a central opening, are arranged along the ion optical axis at least in the drift region, and multiple ventilation holes are formed at locations spaced apart by a predetermined distance toward the outer circumference from the central opening in the conductive disc-shaped members of the multiple electric field forming electrodes and in each member forming the shutter gate grid.

Preferably, the ventilation holes are provided at locations far enough away from the central opening so that ion flow does not reach them. The diameter of the central opening is suitably 10 to 30 mm, and the inside diameter of the ventilation holes is 0.5 to 3 mm.

Normally, in the drift region, diffusion gas is made to flow in the opposite direction to the flow of ions, but with the above configuration, diffusion gas flows not just through the central opening but also through the ventilation holes. Thus, diffusion gas can be made to flow substantially uniformly through the inside of the housing in which the drift region is formed, and not just through the central openings of the electrodes. As a result, it is possible to keep the flow velocity of the diffusion gas near the center of the housing through which the ion flow passes from becoming extremely high, allowing the resolution to be increased. Furthermore, since diffusion gas flow is formed also near the walls of the housing, contamination and charge-up of the housing walls can be reduced.

Furthermore, the ion mobility spectrometer according to the present invention may be configured such that the electric field forming electrodes comprise a substantially round tubular first electrode with a flange protruding to the inner circumferential side and a disc-shaped second electrode having a flange central opening, which is fitted inside the round tubular part of the first electrode, wherein the second electrode has multiple notches formed from the outer edge part radially inward, and the portions between circumferentially adjacent notches are bent.

Based on this configuration, the second electrode can be provided with springiness like a spring washer. As a result, the clamping force when securing the second electrode to the flange of the first electrode by means of screws or the like is increased, increasing the mechanical strength. Furthermore, mechanical separation due to differences in the coefficient of thermal expansion between the insulation material and metal under high temperature conditions can be prevented.

Effect of the Invention

With the ion mobility spectrometer according to the present invention, the separation distance between the pair of grid electrodes and the gap between adjacent conductive wires and the like can be determined with high precision while having a simple structure. As a result, for example, the pulse width of ions passing through the shutter gate grid becomes stable, and thus the resolution and precision of analysis become stable. Furthermore, contact between conductive wires to which different voltages are applied can be reliably avoided, thus making it possible to ensure high reliability. Moreover, since the structure is simple and ease of assembly is good, the costs can be reduced. In addition, since the portions exposed to the ions are mainly conductors, charge-up does not occur readily, and thus reduction in analytical precision due to disruption of the electric field caused by charge-up can be prevented.

DETAILED DESCRIPTION OF THE EXEMPLARY EMBODIMENTS

An example of embodiment of the ion mobility spectrometer according to the present invention will be described below with reference to the appended drawings.

Figure 1:
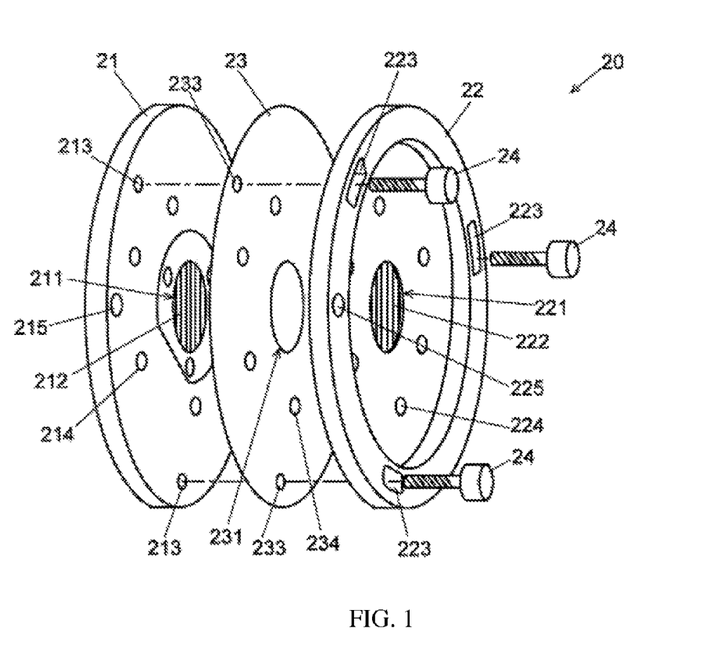
FIG. 1 An exploded perspective view of the shutter gate grid of an ion mobility spectrometer constituting an example of embodiment of the present invention.
Figure 2:
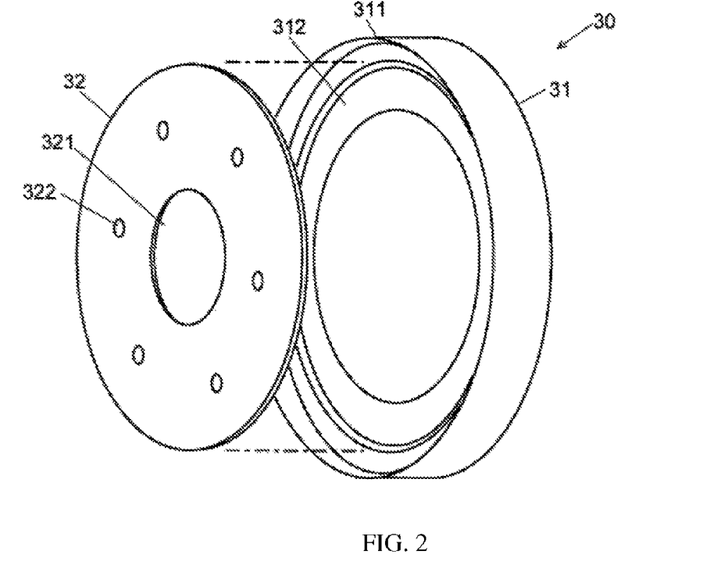
FIG. 2 An exploded perspective view of an electric field forming electrode of the ion mobility spectrometer of the present example of embodiment.
Figure 3:
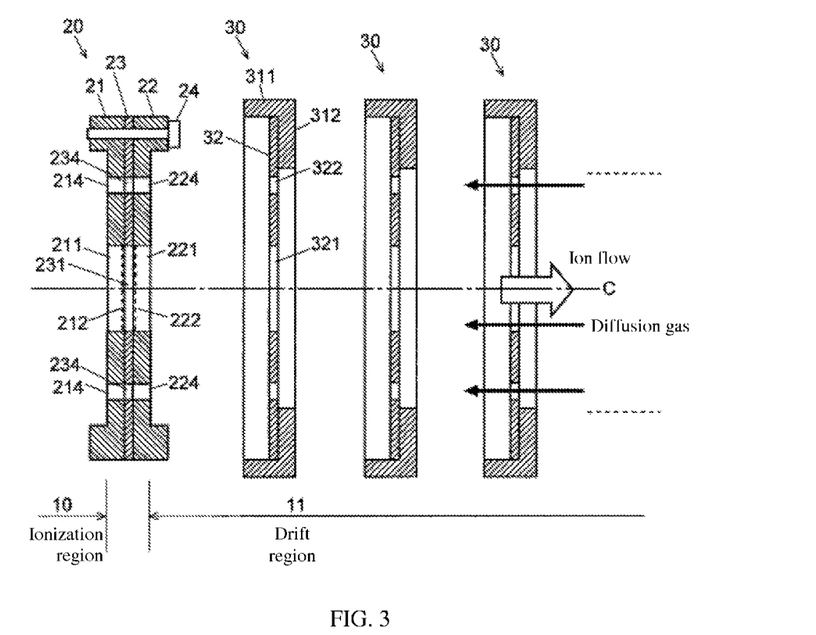
FIG. 3 A schematic diagram of the drift region portion of the ion mobility spectrometer of the present example of embodiment.

FIG. 3 is a schematic cross-sectional view showing the general configuration of the drift region portion of the ion mobility spectrometer of the present example of embodiment; FIG. 1 is an exploded perspective view of the shutter gate grid of FIG. 3; and FIG. 2 is an exploded perspective view of an electric field forming electrode of FIG. 3. The basic configuration of the ion mobility spectrometer of the present example of embodiment is the same as that shown in FIG. 5, the difference being the configuration of the shutter gate grid 20 arranged at the boundary between the ionization region 10 and the drift region 11 and the electric field forming electrodes 30 arranged between the ionization region 10 and the drift region 11.

As shown in FIG. 1 and FIG. 3, the shutter gate grid 20 in the ion mobility spectrometer of the present example of embodiment mainly consists of a somewhat thick first disc-shaped member 21 made of metal (corresponding to the first conductive disc-shaped member of the present invention), a somewhat thick second disc-shaped member 22 likewise made of metal (corresponding to the second conductive disc-shaped member of the present invention), and a thin substantially disc-shaped insulation sheet member 23 made of an insulator such as ceramic.

The first disc-shaped member 21 has a central opening 211 of a predetermined diameter (for example, about 10 to 30 mm), and a gate grid 212, wherein multiple conductive wires are secured in parallel at a predetermined gap, is secured by welding to the central opening 211. Furthermore, threaded holes 213 are formed at predetermined locations in the edge area of the first disc-shaped member 21, and multiple ventilation holes 214 of about 2 mm in diameter are formed at locations spaced a predetermined distance away from the edge of the central opening 211 in the direction of the outer circumference.

The second disc-shaped member 22 has a central opening 221 of the same inside diameter as the central opening 211 of the first disc-shaped member 21, and a gate grid 222, wherein multiple conductive wires are secured in parallel at a predetermined gap, is secured by welding to the central opening 221. Furthermore, fan-shaped screw insertion holes 223 are formed at predetermined locations in the edge area of the second disc-shaped member 22, and multiple ventilation holes 224 are formed at locations spaced a predetermined distance away from the edge of the central opening 221 in the direction of the outer circumference.

The insulation sheet member 23 has a central opening 231 with an inside diameter that is the same as or slightly larger than that of the central openings 211 and 221. Furthermore, screw insertion holes 233 are formed at predetermined locations in the edge area of the insulation sheet member 23, and multiple ventilation holes 234 are formed at locations spaced a predetermined distance away from the edge of the central opening 231 in the direction of the outer circumference.

The threaded holes 213 of the first disc-shaped member 21, the screw insertion holes 223 of the second disc-shaped member 22 and the screw insertion holes 233 of the insulation sheet member 23 are provided at locations aligned in the radial direction of the respective member and in the direction of rotation (circumferential direction). Thus, as shown in FIG. 1, in a state where the insulation sheet member 23 has been sandwiched between the first disc-shaped member 21 and the second disc-shaped member 22, insulative screws 24 made of ceramic or the like, which have been inserted through the fan-shaped screw insertion holes 223 of the second disc-shaped member 22, are passed through the screw insertion holes 233 of the insulation sheet member 23 and screwed into the threaded holes 213 of the first disc-shaped member 21, thereby allowing the respective members to be secured. Furthermore, in a state where the three members 21, 22 and 23 have been secured with the insulative screws 24, the ventilation holes 214, 224, 234 of these three members will be at locations aligned in the radial direction of the respective members and in the direction of rotation (circumferential direction), ensuring a ventilation path through these ventilation holes 214, 224, 234.

Furthermore, in a state where the three members 21, 22 and 23 have been secured with the insulative screws 24 as described above, the conductive wires stretched across the central opening 221 of the first disc-shaped member 21 and the conductive wires stretched across the central opening 221 of the second disc-shaped member 22 will be substantially parallel and arranged such that wires of one member are located right in the middle of the wires of the other member, as shown in FIG. 6, and it will be possible to adjust for precise parallelism when securing with the insulative screws 24. Namely, since the screw insertion holes 223 of the second disc-shaped member 22 are fan-shaped and have play in the direction of rotation, in a state where the insulative screws 24 have been slightly tightened, the second disc-shaped member 22 can be turned within a predetermined angular range in relation to the first disc-shaped member 21. Thus, when a worker assembles the shutter gate grid 20, by tightening the insulative screws 24 after appropriately turning the second disc-shaped member 22 so as to finely adjust the position, the conductive wires of the gate grid 212 of the first disc-shaped member 21 and the conductive wires of the gate grid 222 of the second disc-shaped member 22 can be made precisely parallel and positioned at alternating locations.

Furthermore, in a state where the three members 21, 22, 23 have been integrally joined by tightening the insulative screws 24, as described above, the gap between the conductive wires of the gate grid 212 of the first disc-shaped member 21 and the conductive wires of the gate grid 222 of the second disc-shaped member 22 (gap d in FIG. 5) is determined by the thickness of the insulation sheet member 23.

Thus, with the ion mobility spectrometer of the present example of embodiment, the gap and parallelism of the front grid electrode and rear grid electrode, the gap between the conductive wires and the like in the shutter gate grid 20 can be set with high precision.

If, rather than spacing the front grid electrode and the rear grid electrode apart at a distance equivalent to the thickness of the insulation sheet member 23, one wishes to position the two gate grids 212, 222 substantially in the same plane, the inside diameter of the central opening 231 of the insulation sheet member 32 is increased and the inside diameter (the outer shape of the conductive wire portion) of at least one of the central openings of the two disc-shaped members 21, 22 is made slightly (for example, about 1 mm) smaller than the inside diameter of the central opening 231 of the insulation sheet member 23. This makes it possible to arrange the gate grid of one of the disc-shaped members inside the central opening 231 of the insulation sheet member 23. As a result, the two gate grids 212, 222 can be arranged substantially within the same plane regardless of the thickness of the insulation sheet member 23.

In the ion mobility spectrometer of the present example of embodiment, as shown in FIG. 3, when the shutter gate grid 20 opens, ions pass through the central openings 211, 221, 231 of the three members 21, 22, 23, but the area where charge-up can occur near the location of ion passage is only the edge region of the central hole 231 of the insulation sheet member 23. Thus, charge-up does not occur readily in this shutter gate grid 20, and various problems due to charge-up can be resolved, such as the problem of time-consuming conditioning upon startup of the device, proneness to adhesion of contamination, and reduction of ion throughput efficiency due to disruption of electric field.

Furthermore, with the shutter gate grid 20 shown in FIG. 1, threaded holes 215, 225 for electric wiring are provided separately from the threaded holes 213, etc. in the edge area of the first disc-shaped member 21 and second disc-shaped member 22. Electric wiring cables can be secured to these threaded holes 215, 225 by means of crimp terminals or the like, thereby improving the work efficiency of assembly of the device.

As shown in FIG. 2 and FIG. 3, the electric field forming electrodes 30 comprise a metal ring electrode 31 (corresponding to the first electrode of the present invention) with a flange 312 formed extending toward the inside circumference from a flat round tubular portion 311, and a substantially disc-shaped metal sub-ring electrode 32 (corresponding to the second electrode of the present invention) having a central opening 321. Multiple ventilation holes 322 of about 2 mm in diameter are formed at locations spaced a predetermined distance toward the outer circumference from the edge of the central hole 321 of the sub-ring electrode 32 (corresponding to the second electrode of the present invention). The outside diameter of the sub-ring electrode 32 is slightly larger than the inside diameter of the flat round cylindrical part 311 of the ring electrode 31, and the sub-ring electrode 32 is secured with unillustrated screws to the flange 312 of the ring electrode 31. Alternately, the whole electrode is secured in a sandwiched state by means of the frontmost and rearmost flanges.

As shown in FIG. 3, the ions in the drift region 11 pass through the central opening 321 of the sub-ring electrode 32. Furthermore, diffusion gas at a predetermined flow rate is made to flow in the opposite direction to the ion flow, and the diffusion gas, in addition to passing through the central opening 321 of the sub-ring electrode 32 in each electric field forming electrode 30, also flows in the opposite direction to the ions through the ventilation holes 322 formed in the sub-ring electrode 32. Furthermore, in the shutter gate grid 20 formed by integrally joining the three members 21, 22 and 23, ventilation channels are provided by means of ventilation holes 214, 224, 234 at positions spaced away from the central opening toward the outer circumference, so diffusion gas flows through these ventilation channels from the drift region 11 side toward the ionization region 10 side. These ventilation holes 322 and the ventilation channels based on ventilation holes 214, 224, 234 are provided at locations sufficiently removed toward the outer circumference from the edge of the central opening through which the ions pass, and thus the flow of diffusion gas through such ventilation holes and ventilation channels can make the flow of diffusion gas inside the housing close to uniform without biasing it only toward the center. As a result, it is possible to prevent the flow velocity of the diffusion gas near the housing center from becoming very high, making it possible to ensure high time resolution. Moreover, since the diffusion gas can readily flow near the walls of the housing, there is also the effect of reducing charge-up of the walls and adhesion of other contamination.

Figure 4:
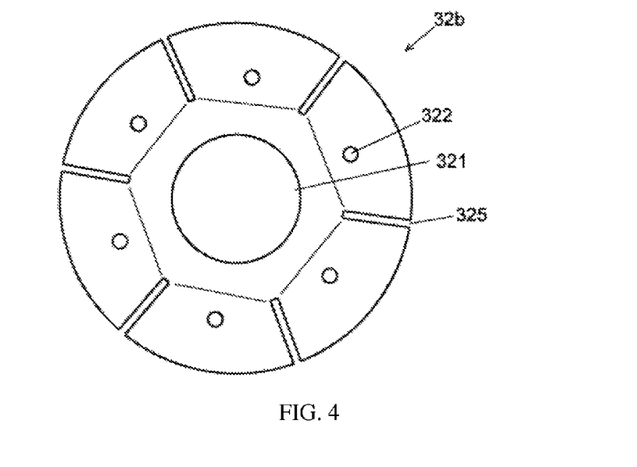
FIG. 4 A plan view showing a modified example of the sub-ring electrode used in the ion mobility spectrometer of the present example of embodiment.

In the above example of embodiment, the sub-ring electrode 32 had a simple disc shape, but this sub-ring electrode may also be made into a shape as shown in FIG. 4. In the sub-ring electrode 32b shown in FIG. 4, multiple notches 325 are formed radially from the edge toward the inner circumference of a disc-shaped metal plate. In this example, notches 325 have been formed at six locations at intervals of an approximately 60° angle of rotation, but this number is arbitrary. Furthermore, the portions between notches 325 adjacent in the direction of rotation are slightly bent either outward or inward in FIG. 4, in alternating fashion along the direction of rotation. Namely, this sub-ring electrode 32b is not entirely flat but is rather in a state where the portions between adjacent notches 325 jut out forward or rearward due to bending. As a result, the sub-ring electrode 32b can be imparted with springiness like that of a spring washer, and the clamping force when securing with screws or the like increases. Consequently, the mechanical strength of the electric field forming electrodes 30 increases and the robustness of the device improves. Furthermore, mechanical separation due to differences in coefficient of thermal expansion between the insulation material and the metal under high temperature conditions can be prevented.

It should be noted that the above example of embodiment is no more than one example of the present invention, and any modifications, corrections or additions made within the gist of the present invention are naturally included within the scope of patent claims of the present application.

For example, the configuration of the ionization region in the ion mobility spectrometer of the example of embodiment described above can be modified at one's discretion, for example, by being replaced with an ion source based on various ionization methods as used in mass spectrometry devices.

Moreover, rather than measuring the mobility of ionized sample molecules, one may also, for example, introduce product ions cleaved through collision-induced dissociation or light-induced dissociation into the drift region and measure their mobility.

It is moreover obvious that the present invention can be applied to an ion mobility spectrometry-mass spectrometry device wherein ions separated according to mobility in the drift region are introduced into a quadrupole mass filter or the like and further separated according to mass-charge ratio before being detected.

DESCRIPTION OF THE REFERENCES

10 . . . ionization region
11 . . . drift region
20 . . . shutter gate grid
21 . . . first disc-shaped member
22 . . . second disc-shaped member
23 . . . insulation sheet member
24 . . . insulative spring
211, 221, 231 . . . central opening
212, 222 . . . gate grid
213 . . . threaded hole
223, 233 . . . screw insertion hole
214, 224, 234 . . . ventilation hole
215, 225 . . . threaded hole for electric wiring
30 . . . electric field forming electrode
31 . . . ring electrode
32 . . . sub-ring electrode
321 . . . central opening
322 . . . ventilation hole

What is claimed:

1. An ion mobility spectrometer comprising an ionization section which generates ions derived from sample components, a drift region which causes the ions generated in the ionization section to move such that they separate according to mobility, and a shutter gate grid for extracting the ions in short pulses and feeding them to said drift region,
   characterized in that said shutter gate grid comprises:
   a first conductive disc-shaped member wherein multiple conductive wires are secured in parallel in a central opening and multiple threaded holes are formed in the periphery; a second conductive disc-shaped member wherein multiple conductive wires are secured in parallel in a central opening and multiple fan-shaped screw insertion holes are formed in the periphery; and an insulation sheet member which has a central opening and multiple screw insertion holes formed in the periphery,
   wherein, in a state where said insulation sheet has been sandwiched between said first conductive disc-shaped member and said second conductive disc-shaped member, these members are integrally joined by means of a plurality of screws having electrical insulative characteristics, which are inserted in sequence through the fan-shaped screw insertion holes of said second conductive disc-shaped member, the screw insertion holes of said insulation sheet member, and into the threaded holes of said first conductive disc-shaped member.

2. An ion mobility spectrometer as described in claim 1, characterized in that the conductive wires in said first and second conductive disc-shaped members are fused on.

3. An ion mobility spectrometer as described in claim 1, characterized in that said first and second conductive disc-shaped members have threaded holes for attaching electric wires.

4. An ion mobility spectrometer as described in claim 1, characterized in that multiple electrodes for forming an electric field, which are conductive disc-shaped members having a central opening, are arranged along the ion optical axis at least in said drift region,
   and multiple ventilation holes are formed at locations spaced apart by a predetermined distance toward the outer circumference from the central opening in the conductive disc-shaped members of said multiple electric field forming electrodes and in each member forming said shutter gate grid.

5. An ion mobility spectrometer as described in claim 4, characterized in that said electric field forming electrodes comprise a round tubular ring electrode with a flange protruding to the inner circumferential side and a disc-shaped sub-ring electrode having a central opening, which is fitted inside the round tubular part of the ring electrode and secured to the flange, wherein the sub-ring electrode has multiple notches formed from the outer edge part radially inward, and the portions between circumferentially adjacent notches are bent.

6. The ion mobility spectrometer as described in claim 1, wherein the multiple conductive wires of the first conductive disc-shaped member and the multiple conductive wires of the second conductive disc-shaped member are aligned in parallel by turning the second conductive disc-shaped member within a predetermined angular range.

7. A method of making an ion mobility spectrometer, the ion mobility spectrometer comprising an ionization section which generates ions derived from sample components, a drift region which causes the ions generated in the ionization section to move such that they separate according to mobility, and a shutter gate grid for extracting the ions in short pulses and feeding them to said drift region, characterized in that said shutter gate grid comprises a first conductive disc-shaped member wherein multiple conductive wires are secured in parallel in a central opening and multiple threaded holes are formed in the periphery; a second conductive disc-shaped member wherein multiple conductive wires are secured in parallel in a central opening and multiple fan-shaped screw insertion holes are formed in the periphery; and an insulation sheet member which has a central opening and multiple screw insertion holes formed in the periphery, the method comprising;

sandwiching said insulation sheet between said first conductive disc-shaped member and said second conductive disc-shaped member, integrally joining said insulation sheet, said first conductive disc-shaped member, and said second conductive disc-shaped member by means of a plurality of screws having electrical insulative characteristics, by inserting the screws in sequence through the fan-shaped screw insertion holes of said second conductive disc-shaped member, the screw insertion holes of said insulation sheet member, and into the threaded holes of said first conductive disc-shaped member, and aligning the multiple conductive wires of the first conductive disc-shaped member and the multiple conductive wires of the second conductive disc-shaped member in parallel by turning the second conductive disc-shaped member within a predetermined angular range.

* * * * *